(12) United States Patent
Ozawa et al.

(10) Patent No.: US 8,437,823 B2
(45) Date of Patent: May 7, 2013

(54) NONINVASIVE LIVING BODY MEASUREMENT APPARATUS AND NONINVASIVE LIVING BODY MEASUREMENT METHOD

(75) Inventors: Toshiyuki Ozawa, Miki (JP); Shigehiro Numada, Kobe (JP); Toshihiko Kodera, Kobe (JP)

(73) Assignee: Sysmex Corporation, Kobe (JP)

( * ) Notice: Subject to any disclaimer, the term of this patent is extended or adjusted under 35 U.S.C. 154(b) by 598 days.

(21) Appl. No.: 12/696,882

(22) Filed: Jan. 29, 2010

(65) Prior Publication Data

US 2010/0130841 A1 May 27, 2010

Related U.S. Application Data

(63) Continuation of application No. PCT/JP2008/063575, filed on Jul. 29, 2008.

(30) Foreign Application Priority Data

Jul. 31, 2007 (JP) .................................. 2007-198669

(51) Int. Cl.
*A61B 5/1455* (2006.01)
(52) U.S. Cl.
USPC ............................ 600/322; 600/324; 600/474
(58) Field of Classification Search .................. 600/310, 600/320, 322, 323, 324, 476
See application file for complete search history.

(56) References Cited

U.S. PATENT DOCUMENTS

| 5,722,398 | A | * | 3/1998 | Ishihara et al. | ................ 600/322 |
| 6,443,928 | B1 | * | 9/2002 | Francis | .......................... 604/116 |
| 7,225,005 | B2 | * | 5/2007 | Kaufman et al. | ............. 600/322 |
| 2004/0162471 | A1 | | 8/2004 | Ikeda et al. | |
| 2007/0015980 | A1 | | 1/2007 | Numada et al. | |

FOREIGN PATENT DOCUMENTS

JP 2007-044491 A 2/2007

OTHER PUBLICATIONS

International Search Report for International Application No. PCT/JP2008/063575, dated Aug. 26, 2008, 3 pages.

* cited by examiner

*Primary Examiner* — Eric Winakur
(74) *Attorney, Agent, or Firm* — Brinks Hofer Gilson & Lione (57) ABSTRACT

An easily wearable noninvasive living body measurement apparatus is provided. The noninvasive living body measurement apparatus (1) is composed of an apparatus body (3) and a wristband (40). The apparatus body (3) is composed of a body section (31) and a body section retention member (4). The body section (31) is retained by the wristband (40) via the body section retention member (4). By allowing the wristband (40) to be attached to a position in the vicinity of a wrist of a forearm of a human, the apparatus body (3) is attached to a human body. An imaging section (5) is retained at a position protruding outside from a width D of the wristband (40). This allows, when the wristband (40) is worn around the arm, the imaging section (5) to be located at a position at which the imaging by the imaging section (5) can be performed.

10 Claims, 13 Drawing Sheets

NONINVASIVE LIVING BODY MEASUREMENT APPARATUS AND NONINVASIVE LIVING BODY MEASUREMENT METHOD

RELATED APPLICATIONS

This application is a continuation of PCT/JP2008/063575 filed on Jul. 29, 2008, which claims priority to Japanese Application No. JP2007-198669 filed on Jul. 31, 2007. The entire contents of these applications are incorporated herein by reference.

TECHNICAL FIELD

The present invention relates to a noninvasive living body measurement apparatus for acquiring living body information by irradiating a living body to image the irradiated living body. The present invention also relates to a noninvasive living body measurement method for acquiring living body information by irradiating a living body to image the irradiated living body.

BACKGROUND ART

There has been known a noninvasive living body measurement apparatus that measures blood components by imaging a living body with the use of an imaging means to analyze a blood vessel in a living body image. The techniques as described above include a noninvasive living body measurement apparatus as disclosed in U.S. Patent Application Publication No. 2004-162471.

According to this noninvasive living body measurement apparatus, a wrist including a blood vessel (vein) is irradiated by a light source to measure blood components based on the image obtained by imaging the irradiated wrist, thereby displaying the measurement result on a display section. In order to image the to-be-measured blood vessel appropriately, the to-be-measured blood vessel must be positioned at a region suitable for the imaging by an imaging section. Thus, the noninvasive living body measurement apparatus disclosed in the above publication generates a blood vessel image showing the to-be-measured blood vessel based on the living body image obtained from the imaging section to display the image on the display section and displays, on the display section, an index showing the region suitable for the imaging by the imaging section, so that the positioning can be performed easily.

By the way, among blood vessels existing in an arm, blood vessels existing in a wrist are particularly suitable for an imaging. The reason is that wrist veins exist at such shallow positions from the skin that allows visual recognition of the veins, the positions cause smaller light scattering in the living body, and the blood vessels have a thick and simple shape, thus allowing the blood vessels to be imaged clearly. The noninvasive living body measurement apparatus disclosed in the publication is configured so that the imaging section is provided just above a wristband. This configuration requires the wristband to be wound around the wrist in order to image the blood vessels existing in the wrist. However, since the wrist includes joints as a movable section, it has been difficult to wear a wristband having an imaging section and having a width.

DISCLOSURE OF THE INVENTION

The present invention has been made in view of the situation as described above. It is an objective of the present invention to provide a noninvasive living body measurement apparatus that can be easily worn while positioning an imaging region at a wrist suitable as an imaging object.

In order to solve the above disadvantages, a noninvasive living body measurement apparatus according to the first aspect of the present invention is characterized in comprising: an apparatus body comprising a light source section for irradiating light to a living body and an imaging section for imaging the irradiated living body; and a wearing section that is configured so as to be able to be worn around an arm of the subject and that retains the apparatus body, wherein the apparatus body is retained by the wearing section so that, when the wearing section is worn around a predetermined position of the arm other than a wrist of the subject, the imaging section is placed over the wrist of the subject.

A noninvasive living body measurement method according to the second aspect of the present invention is characterized in comprising: a step of allocating, on a palm-side of the wrist of the subject, an imaging section of a apparatus body comprising a light source section for irradiating light to a living body and the imaging section for imaging the irradiated living body by wearing a wearing section around a predetermined position other than a wrist of an arm of a subject; a step of irradiating the palm-side of the wrist by using the light source section; a step of imaging the palm-side of the irradiated wrist by using the imaging section; and a step of obtaining living-body information by analyzing an image obtained through the imaging step.

By including the configuration as described above, the present invention can image the wrist that is a suitable portion as a to-be-measured portion while allowing the noninvasive living body measurement apparatus to be worn around the arm. Since the arm has a fixed periphery length and has a simple shape when compared with a wrist joint, the apparatus can be worn around the arm easily. Furthermore, since the arm has a fixed periphery length, the apparatus attached to the arm is suppressed from being dislocated. Thus, the noninvasive living body measurement apparatus according to the present invention can provide measurement in a stable manner.

DETAILED DESCRIPTION OF THE PREFERRED EMBODIMENTS

The following section will describe in detail, with reference to the attached drawings, embodiments of a noninvasive living body measurement apparatus and a noninvasive living body measurement method of the present invention.

Figure 1:
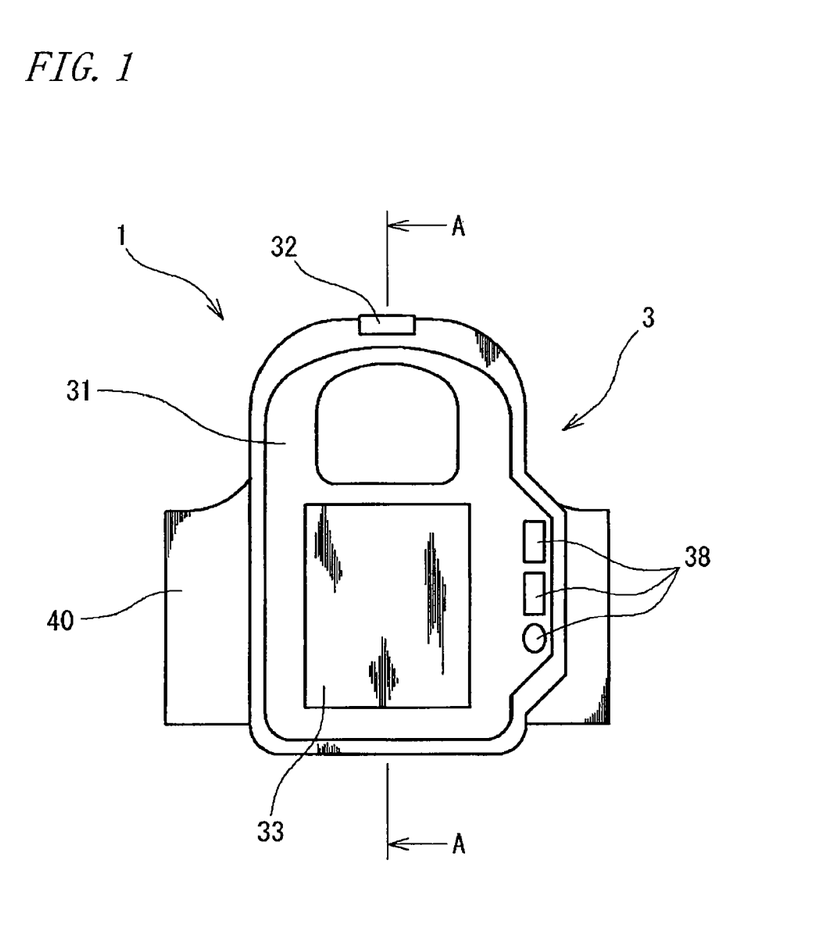
FIG. 1 is a plan view illustrating a noninvasive living body measurement apparatus according to the first embodiment.
Figure 2:
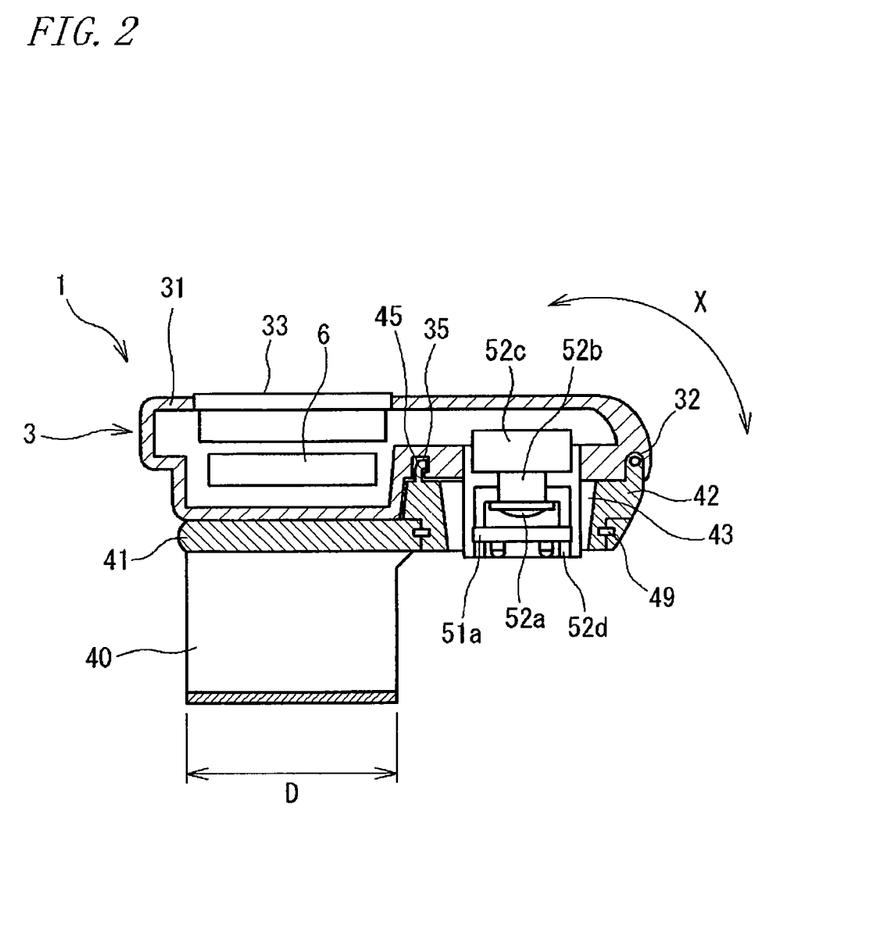
FIG. 2 is a cross-sectional view of FIG. 1 seen in the direction of the arrow A-A.
Figure 3:
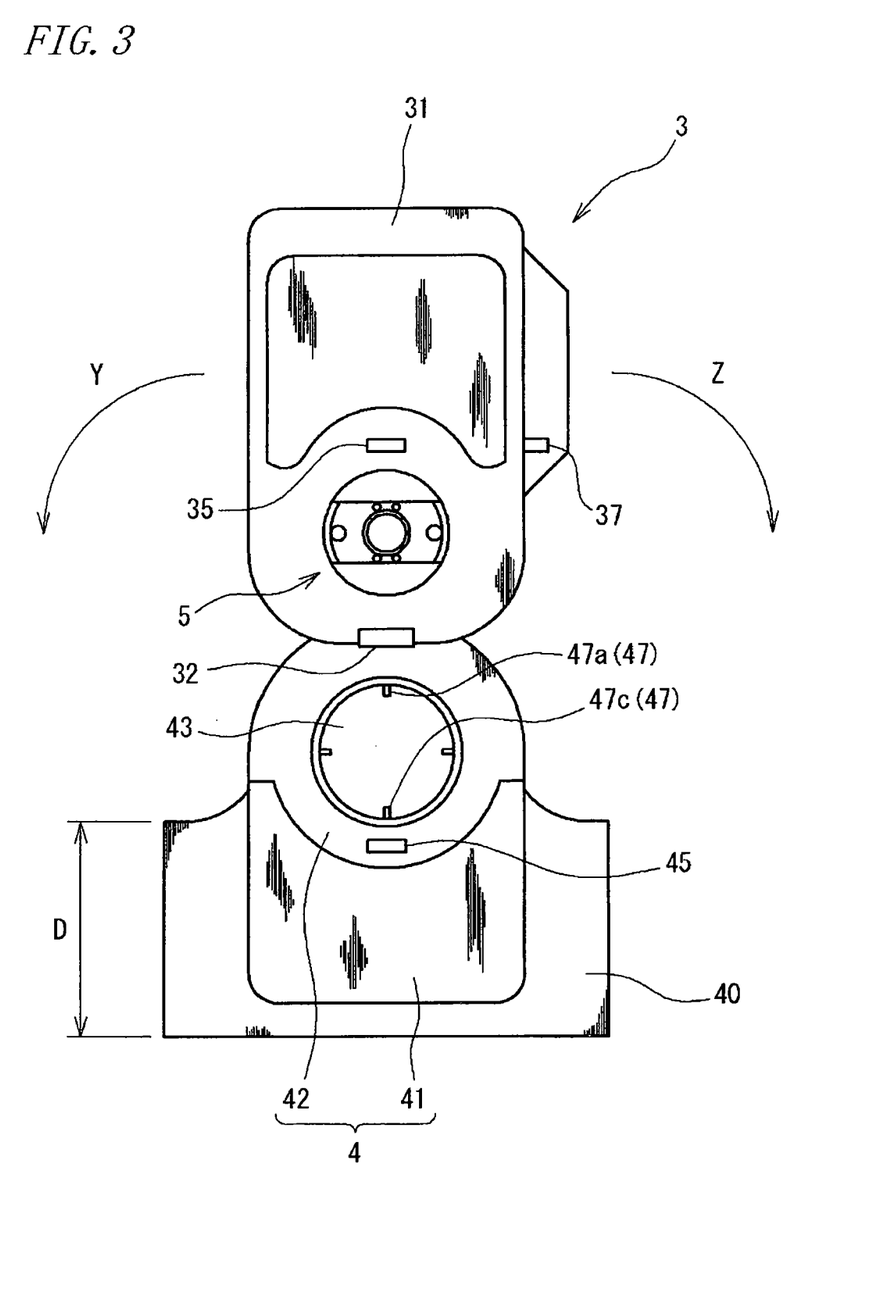
FIG. 3 is a plan view illustrating a noninvasive living body measurement apparatus according to the first embodiment.

FIG. 1 is a plan view illustrating a noninvasive living body measurement apparatus 1 according to the first embodiment of the present invention. FIG. 2 is a cross-sectional view of FIG. 1 seen in the direction of the arrow A-A. FIG. 3 is a plan view illustrating the noninvasive living body measurement apparatus 1. In FIG. 3, an apparatus body 3 is rotated via a hinge member 32.

This noninvasive living body measurement apparatus 1 (hereinafter simply referred to as "apparatus") is a wristwatch-type living body measurement apparatus and is composed of the apparatus body 3 and a wristband 40. The apparatus body 3 is composed of: a body section 31 including an imaging section 5 and an analyzer 6; and a body section retention member 4 retained by the wristband 40. The body section 31 is retained by the wristband 40 via the body section retention member 4. By allowing this wristband 40 to be worn around a human arm, especially a position in the vicinity of a wrist of a forearm, the apparatus body 3 is attached to a human body. The position of the apparatus body 3 can be adjusted by the wristband 40 in the periphery direction of the arm.

As shown in FIG. 1, the body section 31 of the apparatus body 3 has an upper face having a substantially rectangular shape and the center of the upper face has a display section 33. The display section 33 is provided so that the display face thereof is in a direction opposite to the direction of the imaging by the imaging section 5 which will be described later (see FIG. 2). Thus, a user can check the display on the display face while wearing the apparatus 1 so that the wrist can be imaged by the imaging section 5.

One long side of the body section 31 (right long side in FIG. 1) is formed to protrude to the outer side. This protrusion section has an operation section 38 composed of a power source/execution key and a menu key for allowing the user to operate the apparatus 1. Thus, when the user attaches the apparatus 1 to the left arm, the operation section 38 is at a position in front of the user when seen from the user. Thus, the operation can be performed easily.

At the bottom face of the body section 31, the cylindrical imaging section 5 is retained so as to protrude to the lower side. The imaging section 5 includes a light source section 51 and a light-receiving section 52 that are connected by a wiring code or a flat cable (not shown) for example so as to exchange an electric signal with the analyzer 6 and the display section 33. The body section 31 includes therein a layered structure of the analyzer 6 and the display section 33.

The body section retention member 4 is provided between the body section 31 and the wristband 40 (see FIG. 2). The body section retention member 4 is composed of a base stand 41 retained by the wristband 40 and a rotation table 42 retained by the base stand 41. The base stand 41 comprises a plate-like member and one of the longitudinal sides is formed to have a square shape and the other is formed to have a circular arc-like shape. The bottom section of the square shape-side is connected to the wristband 40 and the circular arc-side includes a circular opening for retaining the rotation table 42, which will be described later.

The rotation table 42 comprises a tube-like member having an upper end and a lower end having different outer diameters and has an opening 43 for storing the imaging section 5 provided from the body section 31 in a protruded manner. The lower end of the rotation table 42 is vertically inserted into the opening provided in the base stand 41 and the rotation table 42 is rotatably supported to the base stand 41 around the center of the opening 43. The upper end having a larger diameter than that of the lower end has the hinge member 32 to rotatably support the body section 31 to the rotation table 42. Specifically, the body section 31 can be rotated in the direction shown by the arrow X via the hinge member 32, thus allowing the apparatus 1 to be opened and closed. The body section 31 can be rotated, via the rotation table 42, around the optical axis of a lens 52a of the imaging section 5, which will be described later, in the direction shown by the arrow Y or the arrow Z (see FIG. 2 and FIG. 3).

When the body section 31 is rotated clockwise in the direction shown by the arrow X, the imaging section 5 is disengaged from the opening 43 and the user can visually recognize the blood vessel of a to-be-measured portion via the opening 43. When the body section 31 is rotated in the direction shown by the arrow Y or the arrow Z on the other hand, the imaging section 5 positioned at the center of the opening can be rotated.

The rotation table 42 is made of material that is not optically transmissive. The rotation table 42 is configured so as to be able to block the outside light when the imaging section 5 is used to image a living body image.

A ring-like elastic member 49 is attached to the interface between the base stand 41 and the rotation table 42. The elastic member 49 functions as a retainer for preventing the rotation table 42 from disengaging from the base stand 41 in the upper direction. The elastic member 49 also functions as a friction member that gives an appropriate frictional force between the base stand 41 and the rotation table 42 when the rotation table 42 is rotated.

The wristband 40 is attached to the bottom section of the base stand 41. The wristband 40 is made up of a strip-shaped member such as the Magic Tape® that can be adjusted depending on the thickness of the arm of the user. Alternatively, the wristband 40 also may be made up of an elastic member such as rubber.

From the inner circumference wall of the opening 43 provided in the rotation table 42, there are provided position adjusting members 47 that extend horizontally toward the center of the opening 43 and that comprise a plurality of projections. These position adjusting members 47 are rotated in accordance with the rotation table 42. When the positioning to a blood vessel is performed, the rotation table 42 is rotated so that the blood vessel as the to-be-measured object is positioned on a straight line connecting the position adjusting member 47a provided in the vicinity of the hinge member 32 to the position adjusting member 47c opposed thereto. The straight line connecting the position adjusting members 47a and 47c is directed to pass among light-emitting diodes R1, R2, L1, and L2 in the light source section 51 and is in the same direction as that of the axis AY defining the direction of a region imaged by the imaging section 5 (see FIG. 6). Thus, by adjusting the position adjusting member 47 to be in the same direction as that of the blood vessel, the direction of the imaging section 5 can be adjusted so that the blood vessel can be irradiated from both sides by the light-emitting diodes R1, R2, L1, and L2.

Furthermore, in order to lock the apparatus 1 in a closed state at the measurement, the body section 31 and the rotation table 42 have an engagement hole 35 and an engagement member 45, respectively. The engagement member 45 is provided at a position that is on the upper face of the rotation table 42 and that is opposed to the hinge member 32. The engagement hole 35 is provided at a position that is on the bottom face of the body section 31 and that corresponds to the engagement member 45. The engagement member 45 is vertically raised from the rotation table 42 and the tip end thereof is bent at an angle of about 90 degrees. By locking the tip end of the engagement member 45 to a step section provided in the engagement hole 35, the rotation of the body section 31 in the direction shown by the arrow X is controlled.

A side face of the body section 31 has a cancellation button 37. When this cancellation button 37 is depressed, the engagement of the engagement member 45 with the engagement hole 35 is cancelled to thereby allow the body section 31 to be rotated in the direction shown by the arrow X. Since the engagement member 45 is provided on the rotation table 42, the locking of the engagement member 45 to the engagement hole 35 does not control the rotation of the rotation table 42. Thus, the rotation table 42 can be rotated in the direction shown by the arrow Y or the arrow Z while the apparatus 1 is being closed.

When the apparatus 1 is opened as shown in FIG. 3, the opening 43 storing therein the imaging section 5 is at a position externally protruding from the wristband 40, the width of which is indicated by D. When the apparatus 1 shown in FIG. 3 is closed, then the imaging section 5 is stored in the opening 43 and is retained at a position externally protruding from the wristband 40 (see FIG. 2). By the configuration as described above, the imaging section 5 can image a neighboring part in the distal direction from the portion covered by the wristband 40.

Figure 7:
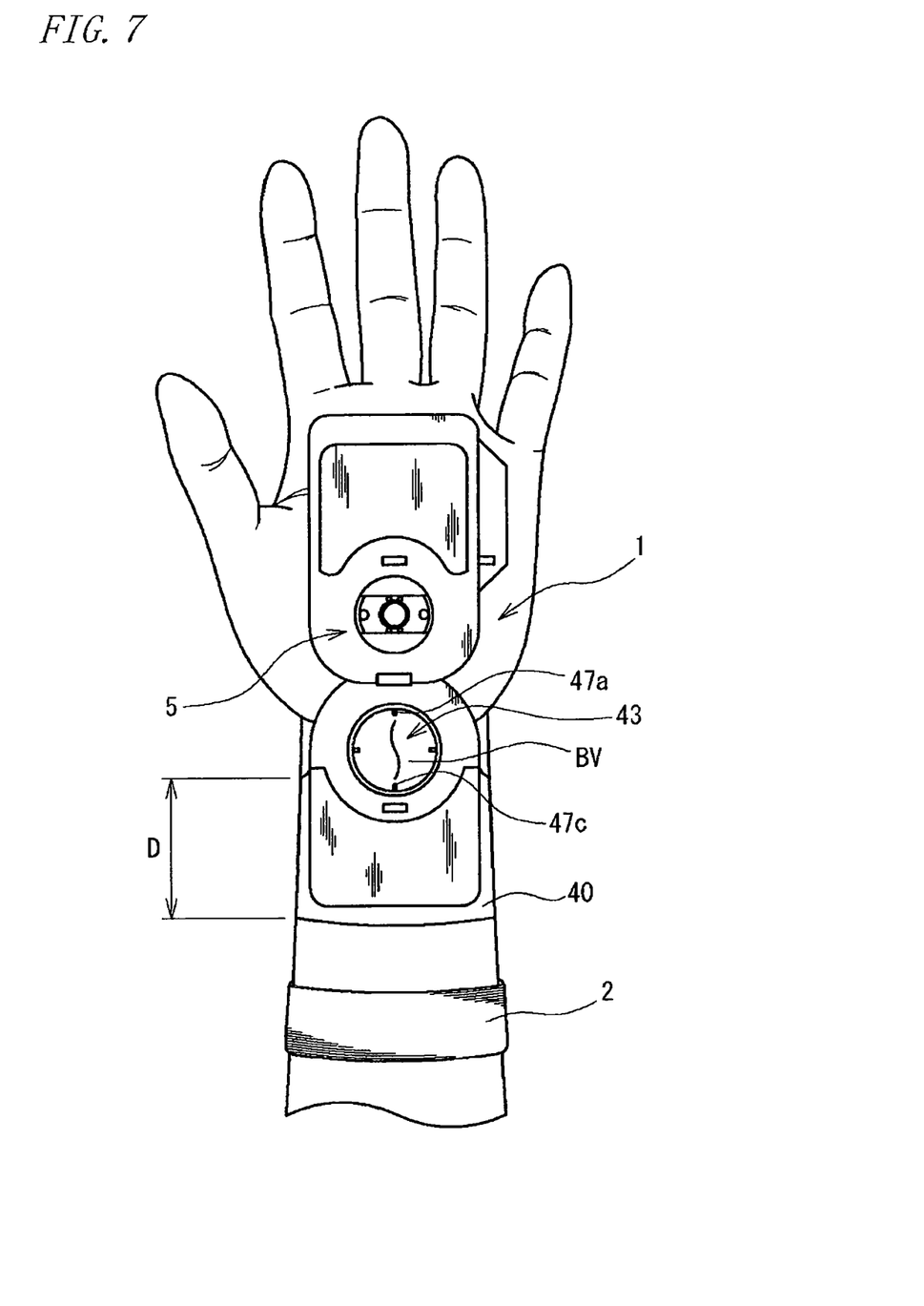
FIG. 7 is a plan view illustrating the noninvasive living body measurement apparatus according to the first embodiment attached to a wrist.

FIG. 7 is a plan view illustrating the apparatus 1 attached to a wrist. When the wristband 40 is worn by the arm as shown, the opening 43 storing therein the imaging section 5 is positioned above the wrist. When the apparatus 1 is closed from the position shown in the figure, the imaging section 5 is abutted on the wrist. Thus, the user can easily fix the wristband 40 to the arm while adjusting its position so that the imaging section is abutted on the wrist suitable as a to-be-imaged portion and thus the wristband 40 can be attached easily. When compared with a wrist, an arm is shaped to have a fixed periphery length that increases as the position is closer to the heart. Thus, even when the imaging section 5 is rotated to be adjusted or is used for measurement, the apparatus 1 is prevented from being dislocated from the fixed position, thus providing a stable measurement.

Figure 4:
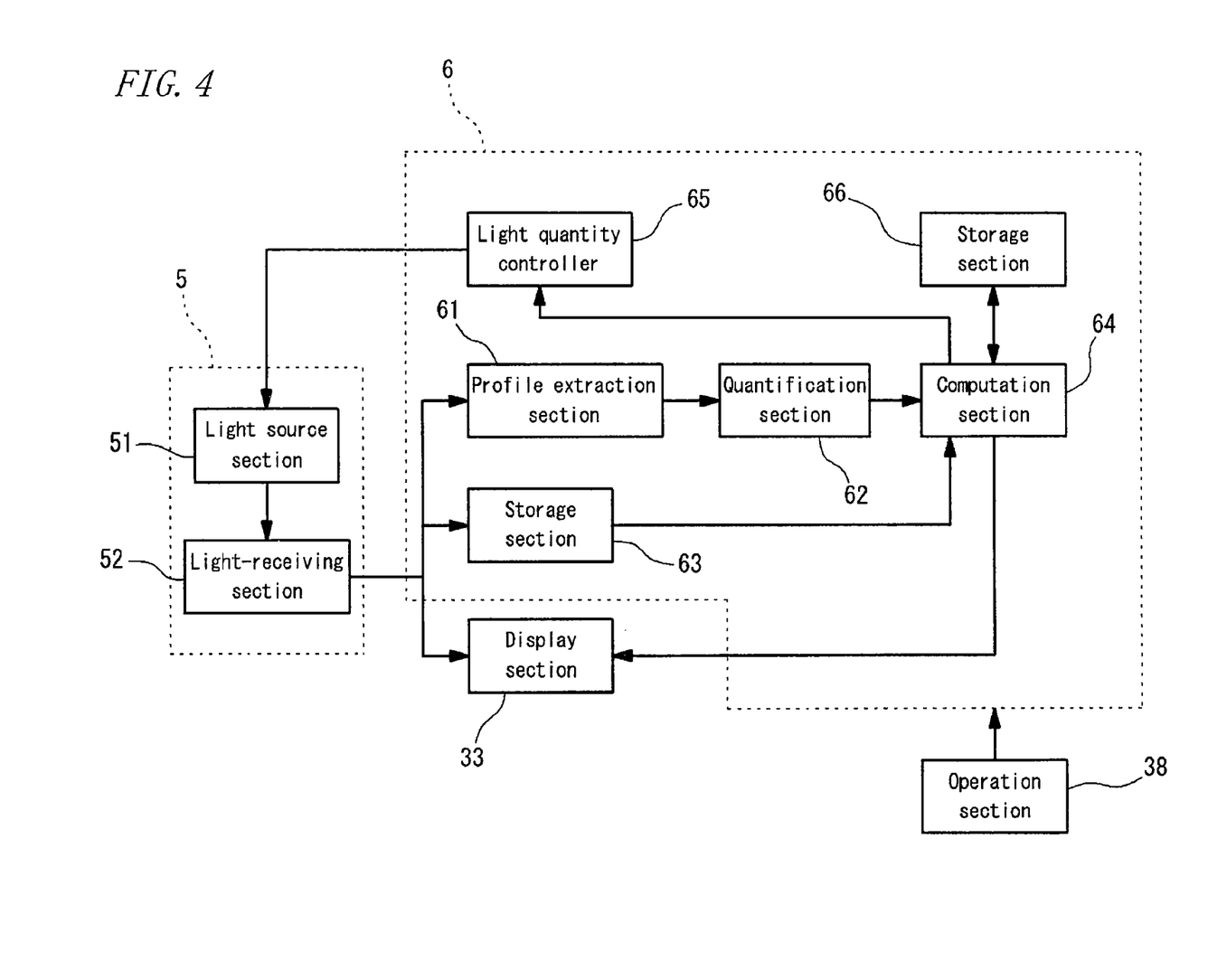
FIG. 4 is a block diagram illustrating the configuration of the noninvasive living body measurement apparatus according to the first embodiment.

FIG. 4 is a block diagram illustrating the noninvasive living body measurement apparatus 1 according to this embodiment. As shown in FIG. 4, the apparatus 1 is composed of: the imaging section 5, the analyzer 6, the display section 33, and the operation section 38. The imaging section 5 is composed of the light source section 51 and the light-receiving section 52. The light source section 51 includes the four light-emitting diodes R1, R2, L1, and L2. The light-receiving section 52 is composed of: a lens 52a for concentrating reflected light to a focal point, a lens tube 52b for fixing the lens 52a, and a CCD camera 52c for taking an image.

Figure 5:
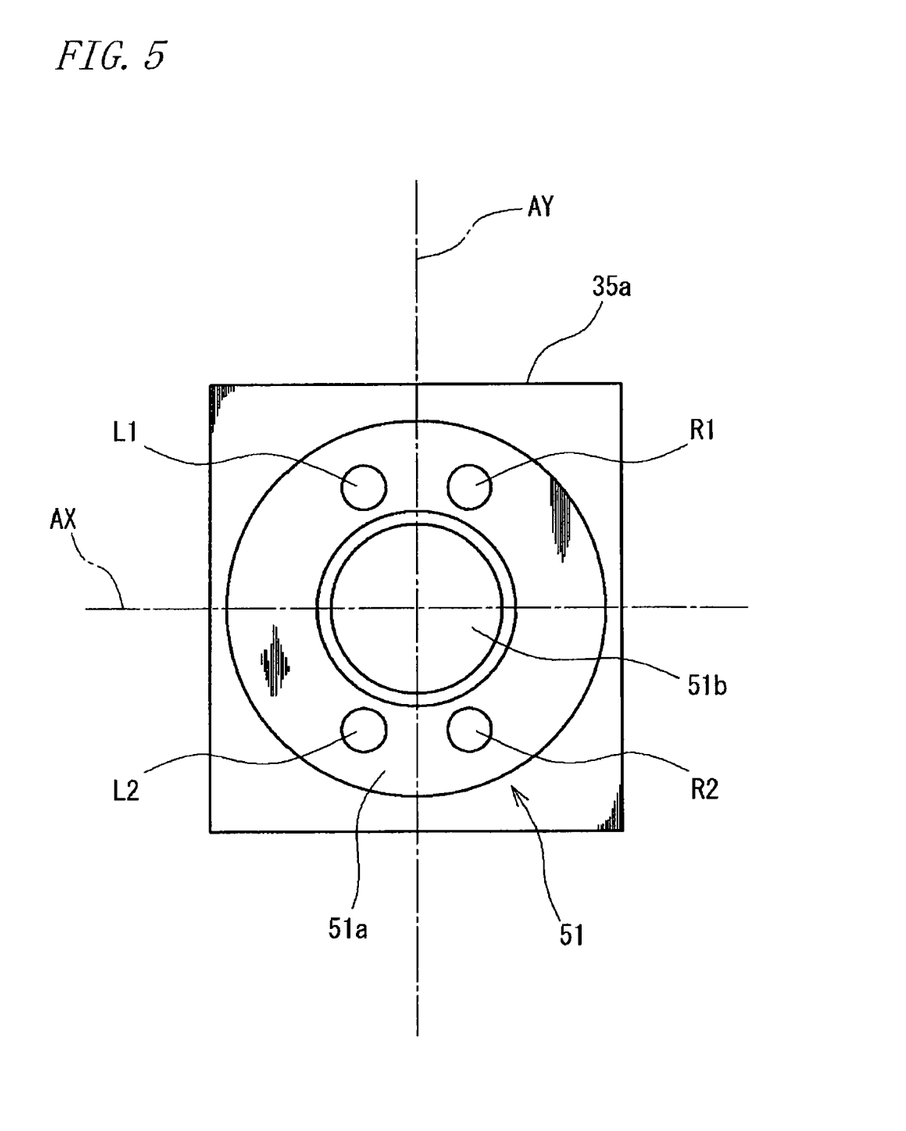
FIG. 5 is a plan view illustrating the configuration of a light source section.

FIG. 5 is a plan view illustrating the configuration of the light source section 51. The light source section 51 is composed of: a circular disc-like retention plate 51a and the four light-emitting diodes R1, R2, L1, and L2 retained by the retention plate 51a. The center of the retention plate 51a has a circular opening section 51b through which light entering the light-receiving section 52 passes. The four light-emitting diodes are disposed along the periphery of this opening section 51b so as to surround the optical axis of the above-described lens 52a.

Figure 6:
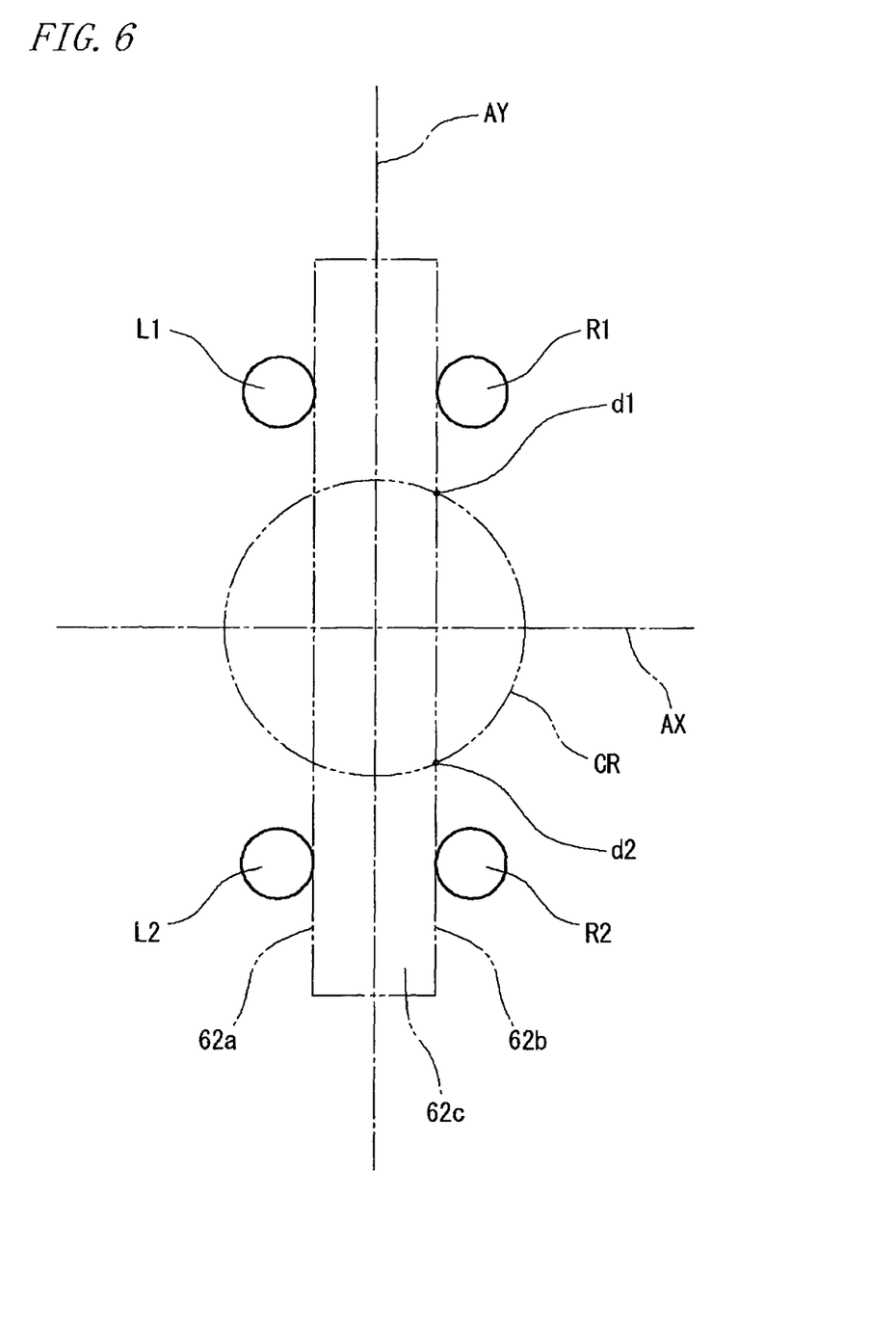
FIG. 6 illustrates positional relation among four light-emitting diodes provided on a retention plate.

FIG. 6 illustrates positional relation among the four light-emitting diodes provided on the retention plate 51a. The light-emitting diodes R1, R2, L1, and L2 are disposed so as to be symmetric to one another with regard to the first axis AY and the second axis AX that pass the center of the opening section 51b and that are orthogonal to each other. More particularly, the light-emitting diodes R1 and L1 are symmetric with regard to the first axis AY. The light-emitting diodes R2 and L2 are similarly symmetric with regard to the first axis AY. The light-emitting diodes R1 and R2 are symmetric with regard to the second axis AX. The light-emitting diodes L1 and L2 are similarly symmetric with regard to the second axis AX.

In a case where the apparatus 1 is being worn around the wrist, the imaging region CR on the surface of the wrist is a region imaged by the light-receiving section 52. The region 62c, which is between an index line 62a at the side of the light-emitting diodes L1 and L2 (the second light source section) and an index line 62b at the side of the light-emitting diodes R1 and R2 (the first light source section), is a region suitable for the imaging by the light-receiving section 52, i.e. a region at which the blood vessel is positioned for the imaging. The index lines 62a and 62b are displayed by the analyzer 6 on the display section 33. In order to analyze the blood components, the position at which the apparatus body 3 is attached is adjusted so that an arbitrarily-chosen blood vessel of the wrist is positioned within the region 62c.

The light-receiving section 52 is composed of: the lens 52a for concentrating reflected light to a focal point; the lens tube 52b for fixing the lens 52a; and a CCD camera 52c for taking an image (see FIG. 2) and can take an image of the imaging region CR. The lens 52a and lens tube 52b are inserted into a cylindrical light-blocking tube 52d having a black interior. The CCD camera 52c takes the formed image to send the image as an image signal to the analyzer 6.

The analyzer 6 is composed of CPU, ROM, RAM, an A/D converter, or a D/A converter for example. The analyzer 6 includes: a profile extraction section 61, a quantification section 62, a storage section 63, a computation section 64, a light quantity controller 65, and a storage section 66. The profile extraction section 61 extracts, with regard to the image taken by the CCD camera 52c of the light-receiving section 52, the image concentration distribution to the second axis AX in the imaging region CR as a brightness profile. The quantification section 62 quantifies the morphological feature of the extracted brightness profile. The storage section 63 converts the optical information obtained from the light-receiving section 52 to digital data and stores the data. The computation section 64 computes the blood component concentration for example based on the quantified feature and the light quantity data. The light quantity controller 65 brings the light quantity of the light source section 51 under an appropriate feedback control based on the information obtained from the light-receiving section 52. The storage section 66 stores the computation result by the computation section 64.

The display section 33 outputs the computation result or a monitor image. The operation section 38 is composed of a menu key and a power source/execution key and is used to operate the ON/OFF control of the power source, to select a function from a display menu, and to start the measurement.

Next, the procedure for positioning the apparatus 1 will be described.

First, as shown in FIG. 7, a pressure bandage 2 such as a cuff (a pressure bandage for measuring a blood pressure) is used to apply a pressure to the arm of the subject to expand the blood vessel (vein) by inhibiting the blood flow in the vessels of the wrist area. Next, while the apparatus 1 is being opened, the wristband 40 is wound around the forearm in the proximity of the wrist. When the apparatus 1 is opened, the to-be-measured portion can be observed through the opening 43. Thus, the user moves the apparatus 1 so that the prominent blood vessel BV appearing in the wrist can be captured via the opening 43.

After the blood vessel BV is captured in the opening 43, the position adjustment is performed by rotating the rotation table 42 in the direction shown by the arrow Y or the arrow Z to position the blood vessel BV within the region 62c (see FIG. 6). Specifically, while observing the prominent blood vessel appearing in the wrist through the opening 43, the rotation table 42 is rotated to the base stand 41 so that the blood vessel BV as a measurement object is positioned on a straight line connecting the position adjusting member 47a and the position adjusting member 47c. When the position adjusting is completed, then the apparatus 1 is closed. As a result, the engagement member 45 provided in the rotation table 42 is engaged with the engagement hole 35 provided in the apparatus body 3 and the apparatus 1 is locked while being closed. Then, measurement is started by allowing the user to operate the power source/execution key of the operation section 38 provided on the upper surface of the body section 31

Next, the following section will describe the measurement operation of the noninvasive living body measurement apparatus 1.

First, when the power source is turned ON through the power source/execution key, the analyzer 6 performs an initialization operation so that an instruction for starting the measurement can be received. When the initialization is completed, the analyzer 6 determines whether the start of the measurement is instructed through the power source/execution key or not. When the analyzer 6 has determined that the start of the measurement is instructed, a measurement processing is started.

When the measurement processing is started, the light quantity controller 65 and the light source section 51 irradiate the measurement region of a part of the living body (a human wrist in this case) including the blood vessel BV at an appropriate light quantity by the light-emitting diodes R1, R2, L1, and L2 (left and right lighting mode). Then, the light-receiving section 52 uses the CCD camera 52c to take an image of irradiated imaging region CR (see FIG. 5). This consequently provides an image of the tissue including the image of the blood vessel (vein) BV within the imaging region CR.

Figure 8:
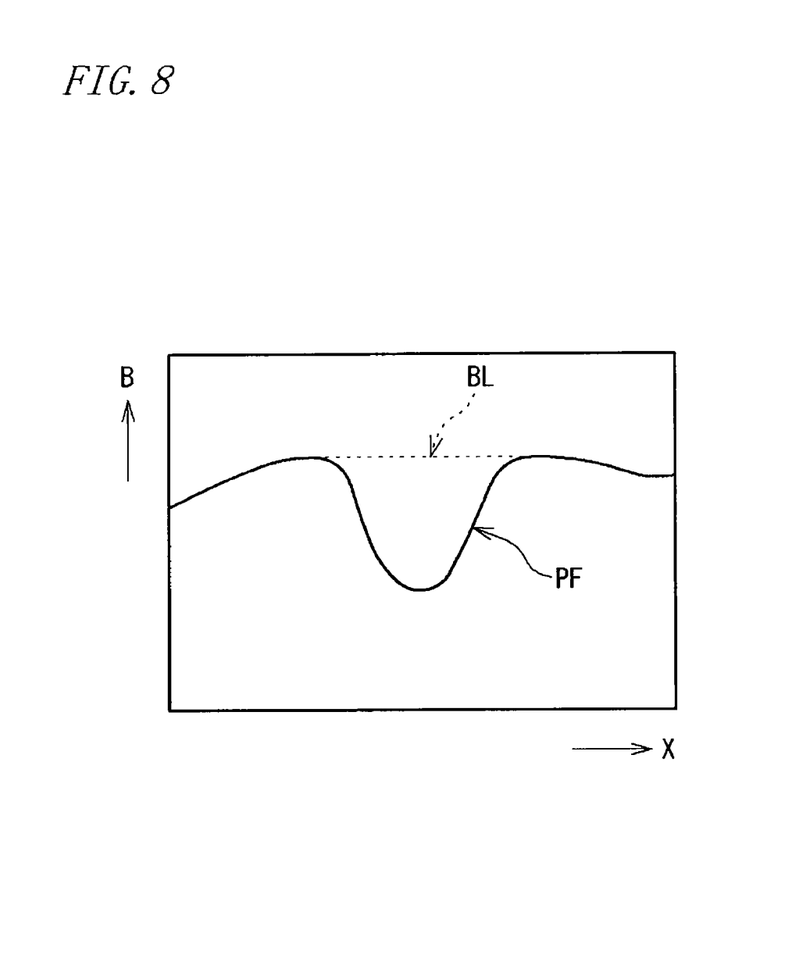
FIG. 8 illustrates the distribution of the brightness B to the position X.

Based on the resultant image, the profile extraction section 61 prepares the brightness profile PF crossing the blood vessel BV (the distribution of the brightness B to the position X) as shown in FIG. 8. Then, the profile extraction section 61 uses the fast Fourier transformation for example to reduce noise components.

Figure 9:
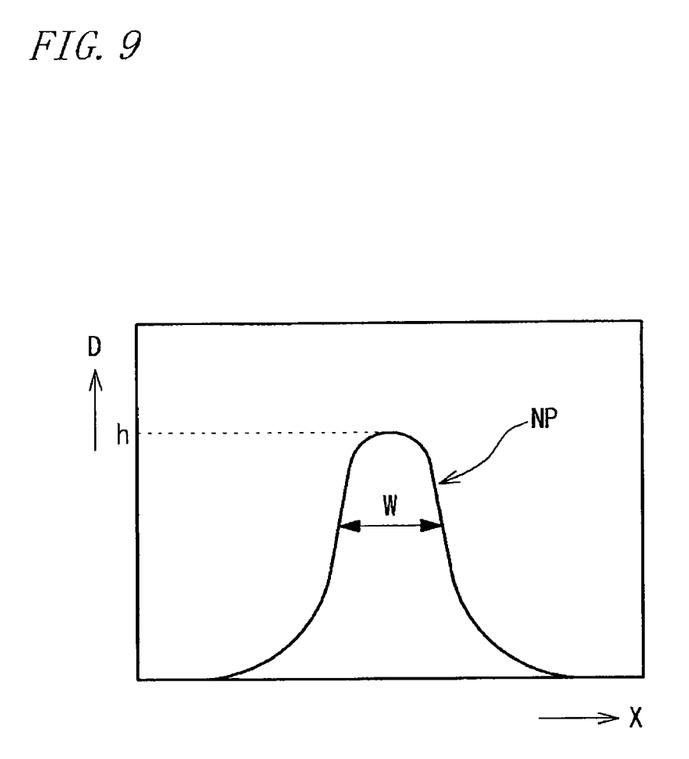
FIG. 9 illustrates the distribution of the concentration D to the position X.

The quantification section 62 normalizes, based on a base line BL, the brightness profile PF obtained through the above process. The base line BL can be obtained based on the shape of the brightness profile PF of the part absorbed by the blood vessel to obtain the concentration profile NP (the distribution of the concentration D to the position X) not depending on the incoming light quantity as shown in FIG. 9.

The computation section 64 calculates, with regard to the normalized concentration profile NP, a peak height h and a half bandwidth w (the width of the distribution of the concentration profile at the position of 50% of the peak height). The resultant value h represents a ratio of the optical intensity of the light absorbed by the to-be-measured blood vessel (blood) to the optical intensity of the light passed through the tissue part. The value w represents a length corresponding to the blood vessel diameter. Then, the computation section 64 calculates, based on the resultant peak height h and half bandwidth w, the uncorrected hemoglobin concentration D based on the following computation formula (1) and stores the result in the storage section 66.

$$D = h/w^n \quad (1)$$

In the formula, n is a constant representing the nonlinearity of the expansion of the half bandwidth due to the scattering. When there is no light scattering, n=1 is established. When there is light scattering, n>1 is established.

Figure 10:
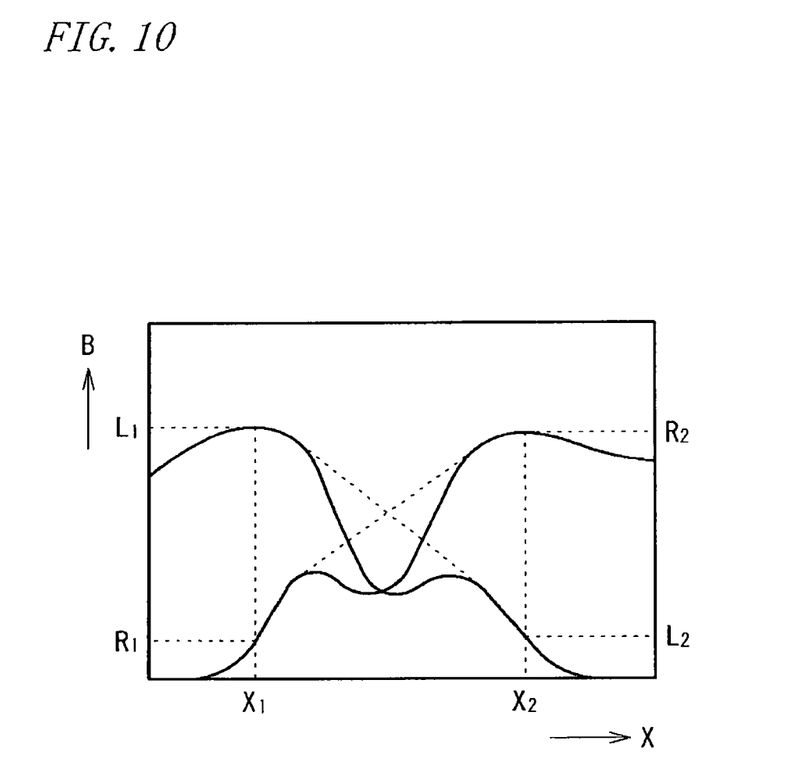
FIG. 10 illustrates the distribution of the brightness B to the position X.

The same portion as the portion imaged in the above process is irradiated by the light-emitting diodes R1 and R2 (right lighting mode) with an appropriate light quantity to thereby image the portion. Then, the portion is irradiated by the light-emitting diodes L1 and L2 (left lighting mode) with an appropriate light quantity to thereby image the portion. The profile extraction section 61 obtains brightness profiles PF1 and PF2 as shown in FIG. 10 with regard to the respective images obtained through these left and right lighting modes.

Figure 11:
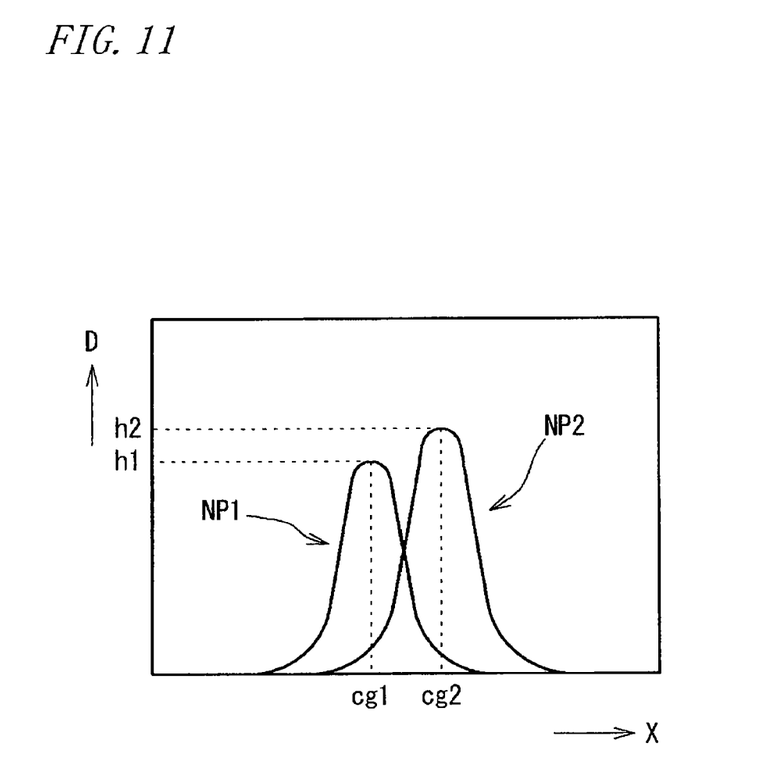
FIG. 11 illustrates the distribution of the concentration D to the position X.

The quantification section 62 obtains, with regard to the brightness profiles PF1 and PF2, concentration profiles NP1 and NP2, neither of which depends on the incoming light intensity (see FIG. 11).

The computation section 64 calculates the peak height h1 and median point coordinates cg1 based on concentration profile NP1 obtained by the irradiation from the light-emitting diodes R1 and R2 and the peak height h2 and median point coordinates cg2 based on the concentration profile NP2 obtained by the irradiation from the light-emitting diodes L1 and L2. Based on the result, the computation section 64 calculates a blood vessel scattering amount index S represented by the following computation formula (2) and stores the calculation result in the storage section 66.

$$S = (cg1 - cg2)/\{(h1 + h2)/2\} \quad (2)$$

Next, the computation section 64 calculates, based on the image of the peripheral tissue of the blood vessel in the resultant image of the living body, a tissue blood amount index M representing the amount of the blood included in the peripheral tissue. Specifically, the distribution of the brightness distributed along the blood vessel image is extracted based on the image of tissue at the periphery of the blood vessel in the living body image, which is at a predetermined distance (e.g., 2.5 mm) from the blood vessel image in the living body image. In the living body image, not only the image of the target blood vessel but also the image of the tissue at the periphery of the blood vessel is included. Since light attenuates in proportion to the blood amount in the tissue, the blood amount in the peripheral tissue can be estimated by calculating the attenuation rate of light in the peripheral tissue.

The computation section 64 derives a correction factor fs based on the blood vessel depth index S calculated through the above process and a correction factor fm based on the tissue blood amount index M. Then, the computation section 64 uses these factors to calculate a corrected hemoglobin concentration $D_0$ represented by the following computation formula (3).

$$D_0 = D \times fs \times fm \quad (3)$$

The storage section 66 stores therein the calculation result described above. The analyzer 6 displays the corrected hemoglobin concentration $D_0$ on the display section 33, thereby completing the measurement processing.

Figure 12:
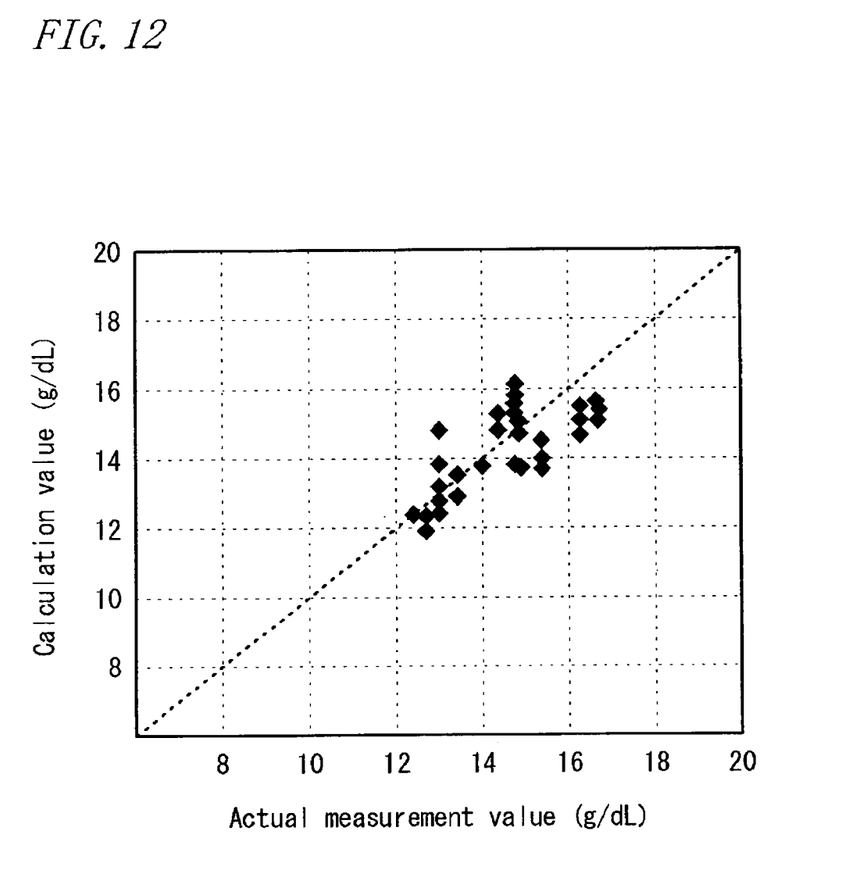
FIG. 12 is a graph plotting, with regard to hemoglobin concentrations of a plurality of subjects, actual measurement values obtained from a blood cell counter for example and calculation values obtained from the noninvasive living body measurement apparatus according to the first embodiment.

FIG. 12 is a graph plotting, with regard to hemoglobin concentrations of a plurality of subjects, actual measurement values obtained from the blood cell counter and calculation values obtained from the apparatus 1 according to the embodiment of the present invention. As shown in FIG. 12, the actual measurement values and the calculation values from the apparatus 1 exist in the vicinity of the straight line having a gradient of 1, and the actual measurement values are not away from the calculation values. This shows that the apparatus 1 can measure the hemoglobin concentration accurately.

In this embodiment, there has been described a configuration in which the hemoglobin concentration as a measurement item is measured. However, the present invention can be widely applied to any item so long as the item is a measurement item that can be measured by imaging the wrist. For example, there can be used a configuration in which the blood vessel of the wrist is continuously imaged at a high speed to thereby measure the blood flow rate.

In this embodiment, there was shown an example was shown in which the apparatus body 3 was attached to the arm using a member such as the wristband 40 that can be worn around the arm. However, the present invention is not limited to the configuration as described above. For example, there can be used a configuration in which the bottom face of the base stand 41 has a plurality of sandwiching pieces and these sandwiching pieces sandwich the arm to thereby attach the apparatus body 3 to the arm.

In this embodiment, there was shown an example in which the analyzer 6 was stored in the body section 31. However, the present invention is not limited to the configuration as described above. There can be used a configuration in which the analyzer 6 is provided outside of the body section 31. For example, a personal computer provided outside of the apparatus 1 is connected to the apparatus 1 wirelessly or by a communication means such as a predetermined connection cable. In this case, the image obtained through the imaging by the imaging section 5 is sent from the communication means to the personal computer and the personal computer analyzes the image and calculates the hemoglobin concentration.

Figure 13:
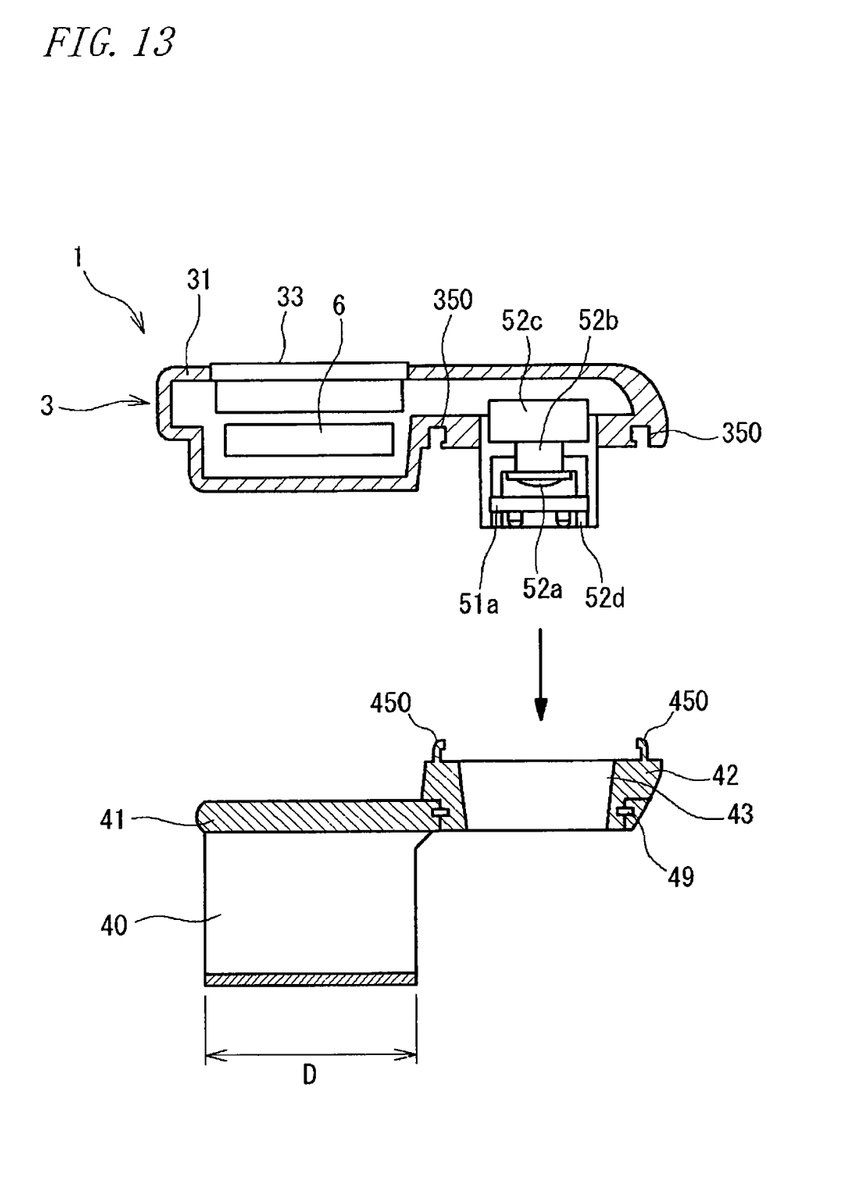
FIG. 13 is a cross-sectional view illustrating the configuration of a noninvasive living body measurement apparatus according to the second embodiment.

FIG. 13 is a cross-sectional view illustrating the configuration of the noninvasive living body measurement apparatus 1 according to the second embodiment. This noninvasive living body measurement apparatus 1 according to the second embodiment has the same configuration as that of the apparatus 1 according to the first embodiment except that the body section 31 is detachably attached to the body section retention member 4 as described later. Thus, the identical constituting elements are denoted with the same reference numerals and will not be described further.

As shown in FIG. 13, the body section retention member 4 includes a pair of lock nails 450 at both of the front and rear ends of the upper part of the rotation table 42. The bottom face of the body section 31 has a pair of engagement holes 350 corresponding to the lock nails 450. By allowing the lock nails 450 to be engaged with the engagement holes 350, the body section 31 is detachably attached to the rotation table 42. By this configuration, the user can detach the apparatus body 3 from the body section retention member 4.

Since the lock nails 450 are provided on the rotation table 42, the rotation table 42 can be rotated to the base stand 41 to thereby rotate the direction of the pair of lock nails 450. The opening 43 has the position adjusting member 47. The user can rotate, while observing the prominent blood vessel appearing in the wrist through the opening 43, the rotation table 42 so that the blood vessel is positioned on the straight line connecting the position adjusting members 47a and 47c. Then, the user may attach the apparatus body 3 to the arm so that the lock nails 450 are engaged with the engagement holes 350.

What is claimed is:

1. A noninvasive living body measurement apparatus comprising:
   an apparatus body comprising a light source section for irradiating light to a living body and an imaging section for imaging the irradiated living body; and
   a wearing band configured to be worn around an arm of the subject and to retain the apparatus body,
   wherein the imaging section comprises an objective lens, and
   the objective lens is arranged such that an optical axis of the objective lens externally protrudes from the wearing band in a width direction of the wearing band.

2. The noninvasive living body measurement apparatus according to claim 1,
   wherein the noninvasive living body measurement apparatus further comprises an analyzing section for analyzing an image obtained by the imaging section, for obtaining living body information, and
   the analyzing section is accommodated in the apparatus body.

3. The noninvasive living body measurement apparatus according to claim 2,
   wherein the living body information is a hemoglobin concentration.

4. The noninvasive living body measurement apparatus according to claim 1,
   wherein the apparatus body comprises a first member retained by the wearing section and a second member that is movably retained by the first member and that accommodates the light source section and the imaging section.

5. The noninvasive living body measurement apparatus according to claim 4,
   wherein the second member is retained by the first member so as to be rotatable around an optical axis of the objective lens.

6. The noninvasive living body measurement apparatus according to claim 4,
   wherein the first member further comprises a connection member, and
   the second member is retained so as to be movable around the connection member.

7. The noninvasive living body measurement apparatus according to claim 6,
   wherein the first member comprises an opening through which a position on the wrist over which the imaging section is placed can be visually recognized, and
   the first member and the second member are configured so that, when the first member is moved around the connection member, the light source section and the imaging section are accommodated in the opening.

8. The noninvasive living body measurement apparatus according to claim 1, wherein the light source section comprises a plurality of light-emitting elements for irradiating a blood vessel existing at the palm-side of the wrist of the subject, and
the imaging section images a blood vessel irradiated by the light-emitting elements.

9. The noninvasive living body measurement apparatus according to claim 1,
wherein the noninvasive living body measurement apparatus further comprises a display section having a display face, and
the display section is provided in the apparatus body so that the display face faces a direction opposite to a direction of the imaging by the imaging section.

10. The noninvasive living body measurement apparatus according to claim 1,
wherein the imaging section configured to image, via the objective lens, a blood vessel existing at the palm-side of the wrist,
the light source section comprises a plurality of light-emitting elements for irradiating a blood vessel to be imaged by the imaging section, the light-emitting elements are placed to surround the optical axis of the objective lens, and
the apparatus body is configured so that the imaging section is movable with respect to the wearing section and the plurality of light-emitting elements and the imaging section are rotatable around the optical axis of the objective lens.

\* \* \* \* \*